US012734056B2

(12) United States Patent
Ichimura

(10) Patent No.: US 12,734,056 B2
(45) Date of Patent: Sep. 15, 2026

(54) MEDICAL TUBULAR BODY DELIVERING DEVICE

(71) Applicant: KANEKA CORPORATION, Osaka (JP)

(72) Inventor: Shizuo Ichimura, Settsu (JP)

(73) Assignee: KANEKA CORPORATION, Osaka (JP)

( * ) Notice: Subject to any disclaimer, the term of this patent is extended or adjusted under 35 U.S.C. 154(b) by 1128 days.

(21) Appl. No.: 17/785,592

(22) PCT Filed: Nov. 19, 2020

(86) PCT No.: PCT/JP2020/043202
§ 371 (c)(1),
(2) Date: Jun. 15, 2022

(87) PCT Pub. No.: WO2021/124786
PCT Pub. Date: Jun. 24, 2021

(65) Prior Publication Data

US 2023/0026765 A1 Jan. 26, 2023

(30) Foreign Application Priority Data

Dec. 18, 2019 (JP) ................................ 2019-228671

(51) Int. Cl.
*A61F 2/95* (2013.01)
*A61F 2/844* (2013.01)
(Continued)

(52) U.S. Cl.
CPC .............. *A61F 2/966* (2013.01); *A61F 2/844* (2013.01); *A61F 2/95* (2013.01); *A61M 2025/018* (2013.01)

(58) Field of Classification Search
CPC .......... A61M 25/0052; A61M 25/0169; A61M 25/0172; A61M 2025/0183;
(Continued)

(56) References Cited

U.S. PATENT DOCUMENTS 8,475,515 B2 * 7/2013 Dorn ....................... A61F 2/966 623/1.11
8,758,421 B2 * 6/2014 Gerdts .................... A61F 2/966 606/191

(Continued)

FOREIGN PATENT DOCUMENTS

JP 2007-97620 A 4/2007
JP 2012-45043 A 3/2012

(Continued)

OTHER PUBLICATIONS

International Search Report, issued in PCT/JP2020/043202, PCT/ISA/210, dated Feb. 9, 2021.

(Continued)

*Primary Examiner* — Sarah W Aleman
(74) *Attorney, Agent, or Firm* — Birch, Stewart, Kolasch & Birch, LLP

(57) ABSTRACT

Provided is a medical tubular body delivering device that can prevent kinking and efficiently deploy a medical tubular body, while maintaining the reinforcing effect without reducing operability. The device has an outer tube through which the medical tubular body is disposed; a guidewire insertion member provided proximal to the medical tubular body; and an inner insertion member provided in the outer tube, and the guidewire insertion member has a penetration passage; a guidewire tube is provided in the penetration passage; the inner insertion member is partially fixed to the guidewire insertion member; a first protection member is provided outside a part of the inner insertion member proximal to a fixing portion; and at least a part of the inner insertion member between a proximal end of the fixing portion and a distal end of a region where the first protection member is provided is covered by a second protection member.

15 Claims, 7 Drawing Sheets

(51) Int. Cl.
*A61F 2/966* (2013.01)
*A61M 25/01* (2006.01)

(58) Field of Classification Search
CPC ... A61M 2025/0177; A61F 2/95; A61F 2/966; A61F 2/2427
See application file for complete search history.

(56) References Cited

U.S. PATENT DOCUMENTS

| | | | | |
|---|---|---|---|---|
| 2006/0259124 | A1 | 11/2006 | Matsuoka et al. | |
| 2008/0255655 | A1* | 10/2008 | Kusleika | A61F 2/91 623/1.11 |
| 2010/0331953 | A1 | 12/2010 | Matsuoka et al. | |
| 2012/0143088 | A1* | 6/2012 | Schultz | A61B 5/6852 604/95.04 |
| 2013/0297012 | A1* | 11/2013 | Willard | A61F 2/2427 623/2.11 |
| 2019/0117938 | A1* | 4/2019 | Norman | A61M 25/0045 |

FOREIGN PATENT DOCUMENTS

| | | | |
|---|---|---|---|
| JP | 2012-55470 | A | 3/2012 |
| JP | 2012-115425 | A | 6/2012 |
| JP | 2016-30033 | A | 3/2016 |

OTHER PUBLICATIONS

Written Opinion of the International Searching Authority, issued in PCT/JP2020/043202, PCT/ISA/237, dated Feb. 9, 2021.

* cited by examiner

[Fig. 1]
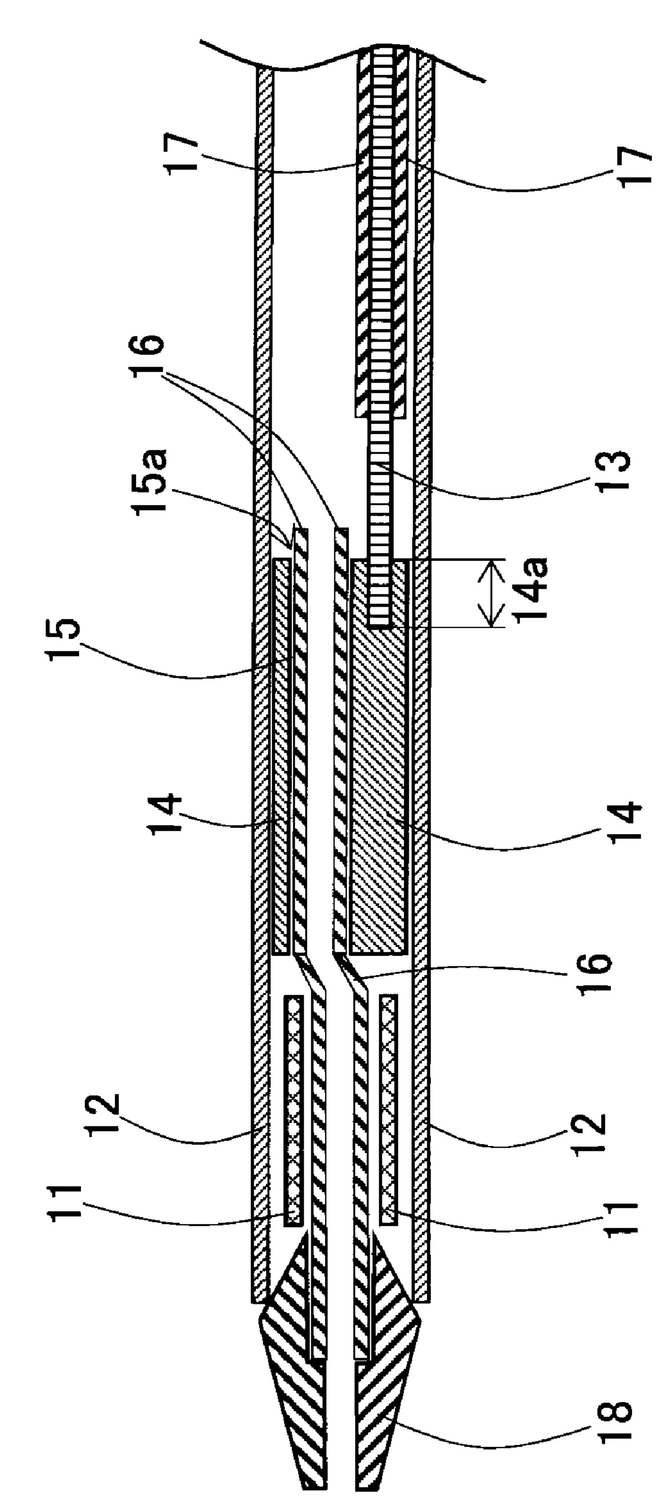

[Fig. 2]
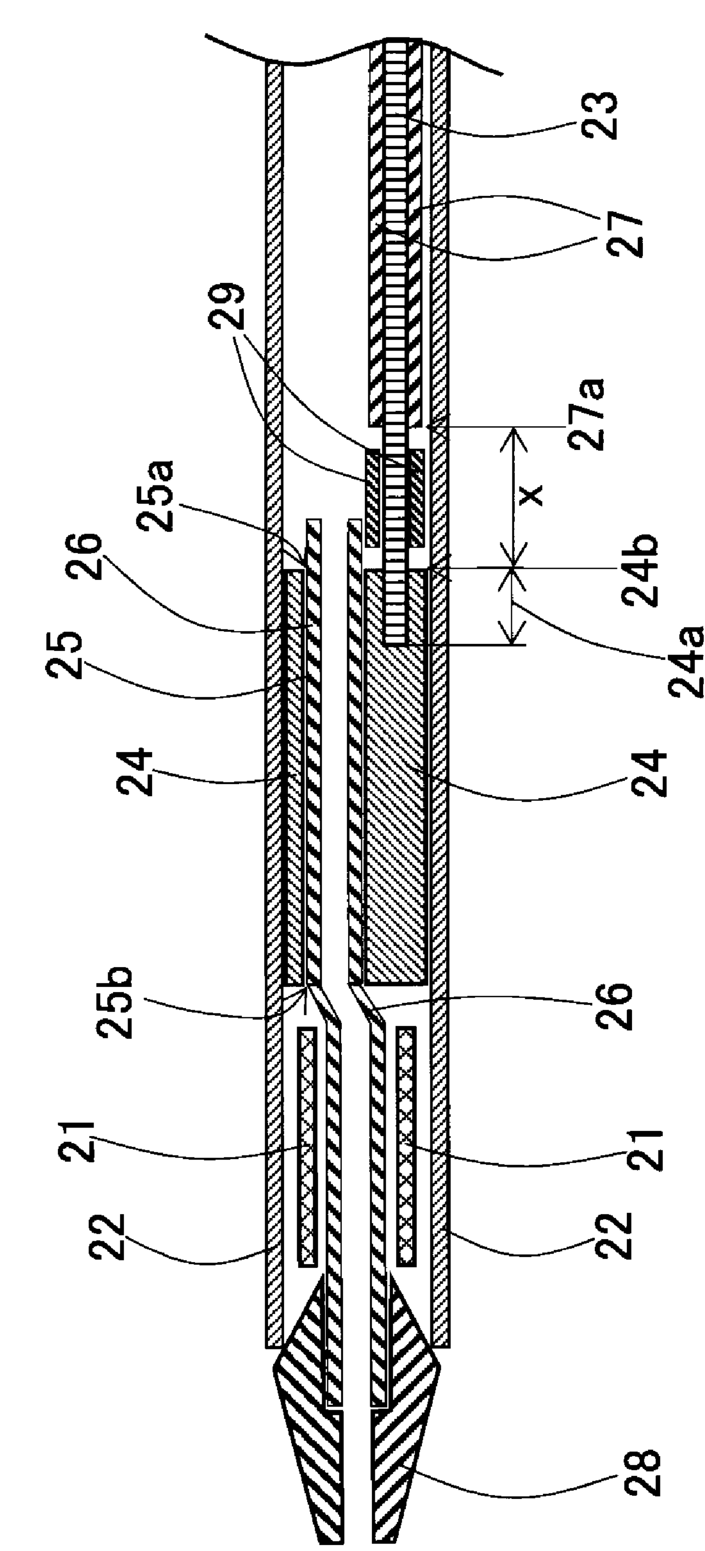

[Fig. 3]
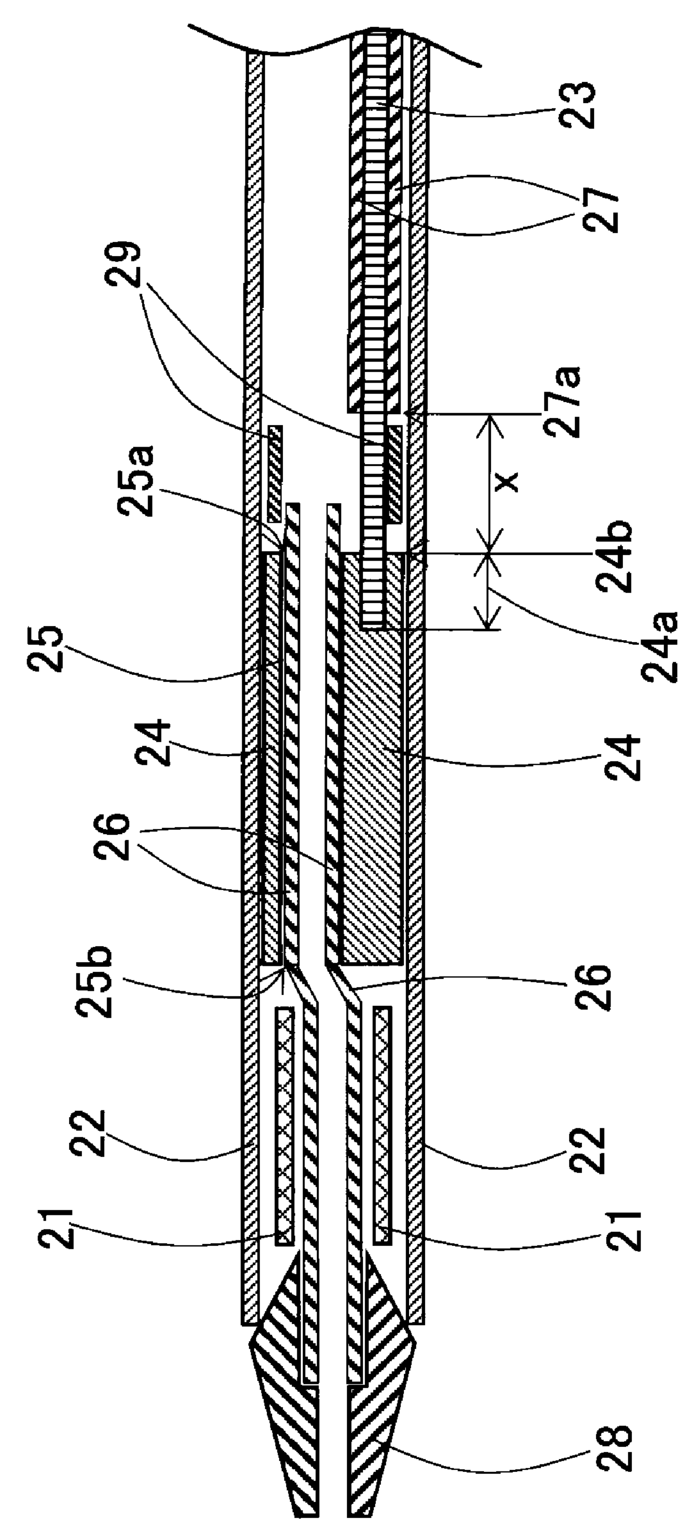

[Fig. 4]
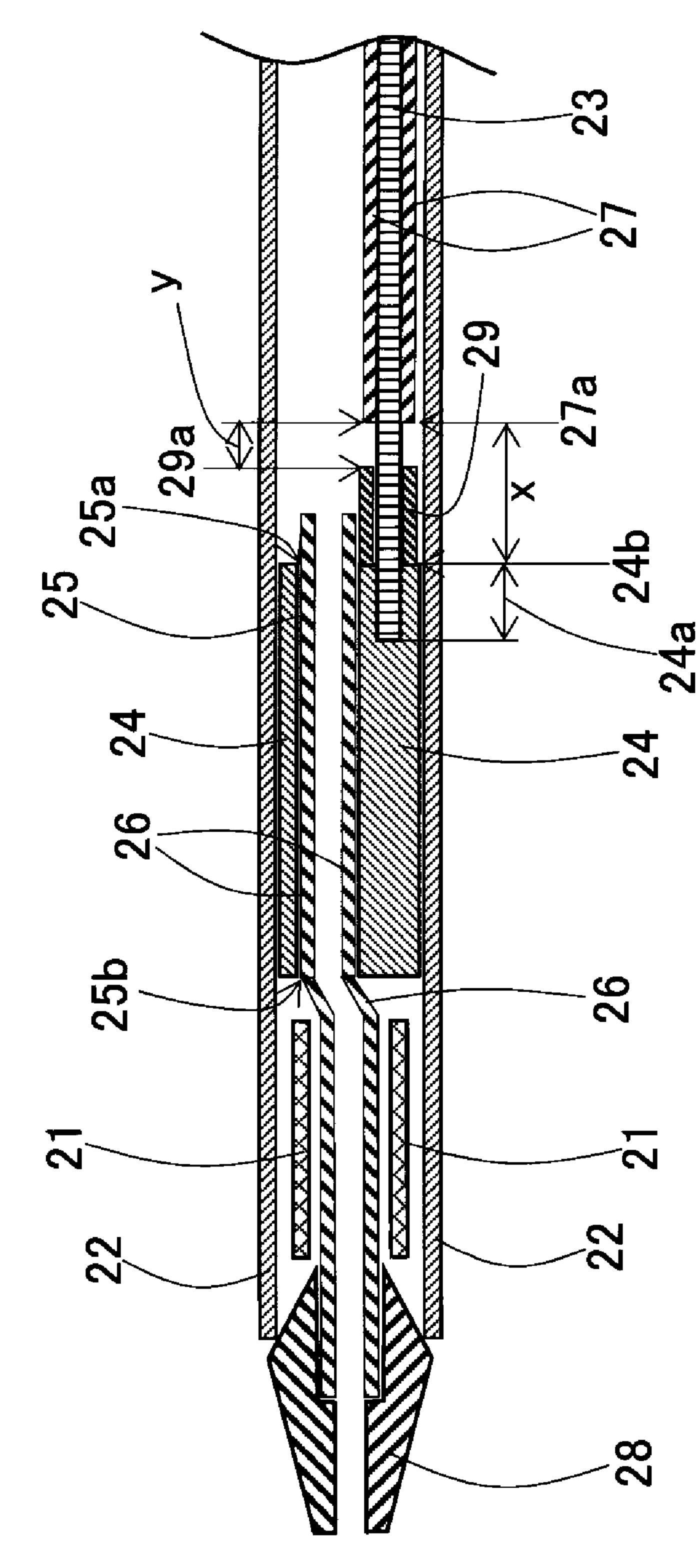

[Fig. 5]
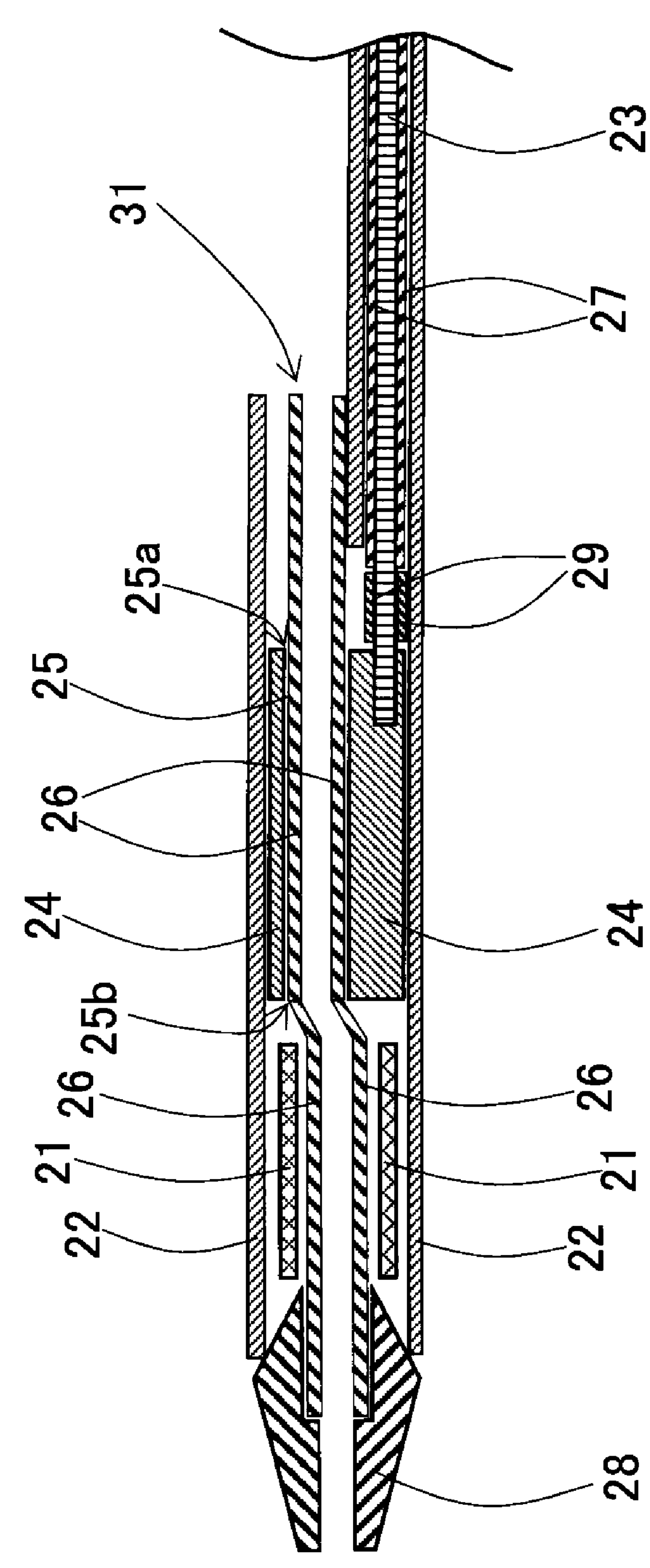

[Fig. 6]
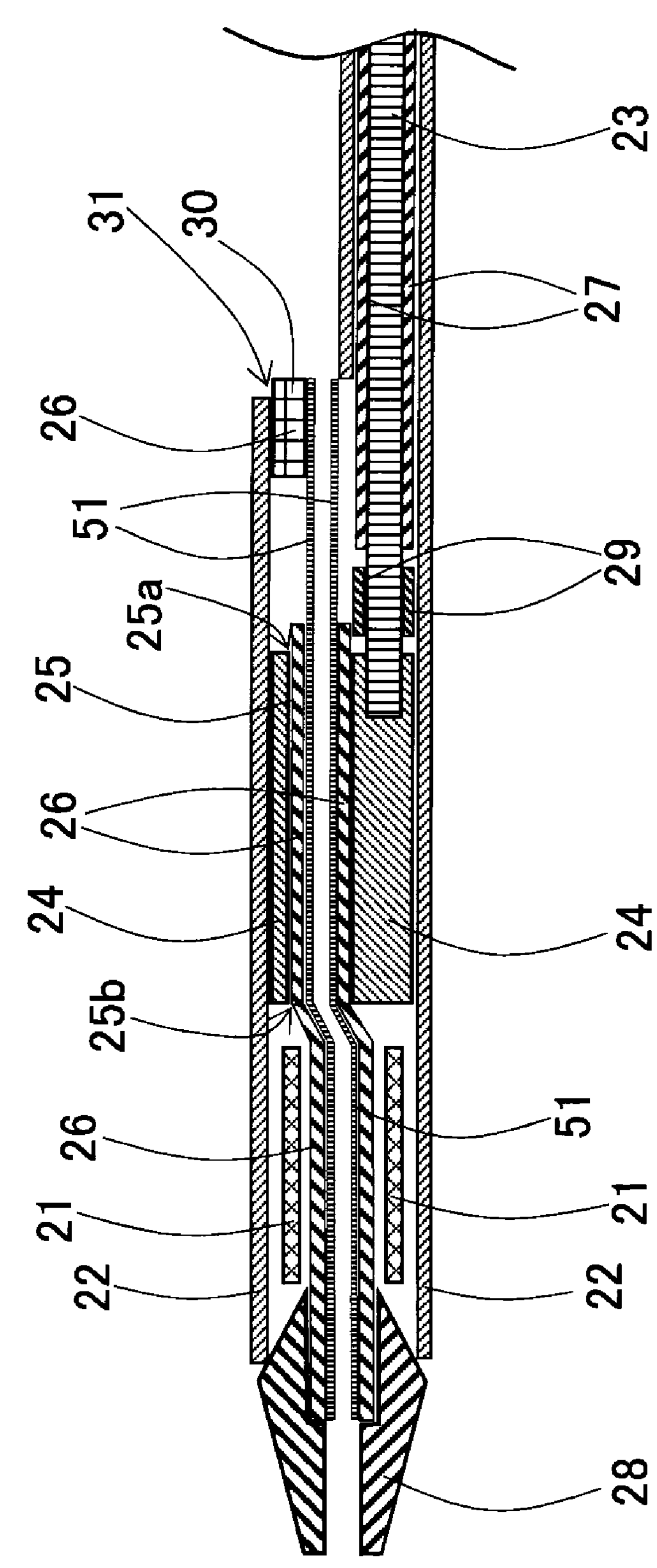

[Fig. 7]
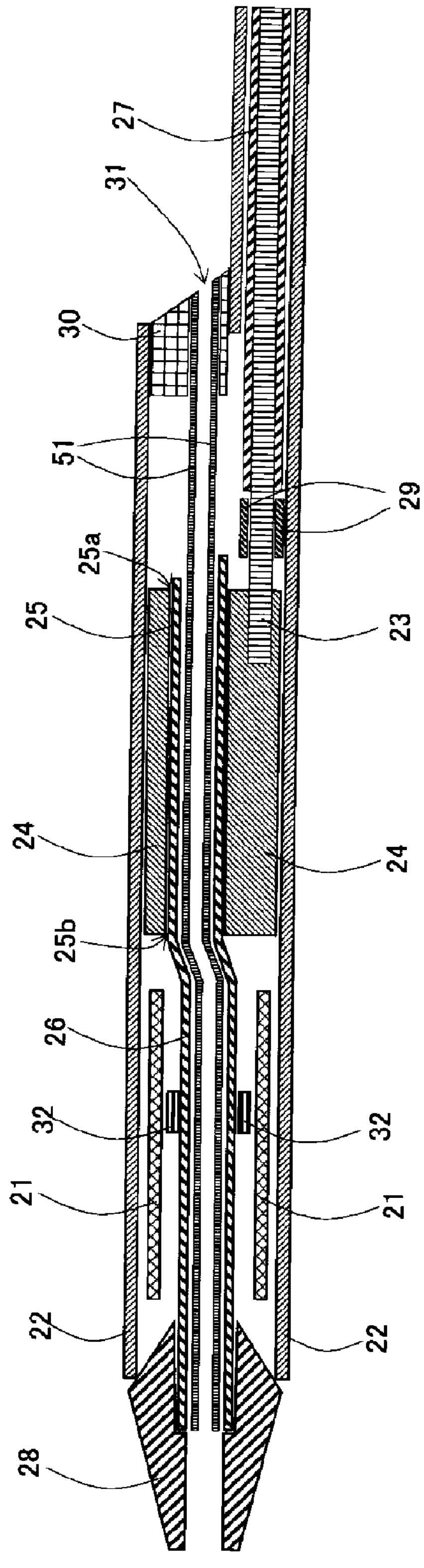

MEDICAL TUBULAR BODY DELIVERING DEVICE

TECHNICAL FIELD

The present invention relates to a medical tubular body delivering device.

BACKGROUND ART

In recent years, minimally invasive treatment techniques have been developed in which a medical tubular body is delivered and placed at a lesion site. The medical tubular body is exemplified by stents, stent grafts, occlusive devices, injection catheters, and prostheses. Of these, stents are generally used to treat various diseases caused by narrowing or occlusion of blood vessels or other lumens of a living body.

In this technique, a delivery device that delivers a medical tubular body to a lesion site through lumens of a living body is used. The delivery device is provided with an outer tube, and the device delivers a medical tubular body to a lesion site through lumens of a living body, keeping the medical tubular body inside the lumen of the outer tube. After delivery, the medical tubular body can be placed at the lesion site by being released from the lumen of the outer tube. Such devices for delivering a medical tubular body are, for example, disclosed in Patent documents 1 and 2.

The devices for delivering a medical tubular body is required to have followability, which enables the operation at hand to be easily transmitted to the distal side, and operability so that the device can enter along the lumen of a living body without resistance, and also required to be resistant to deformation, kinking, and fracture during use. Such a device for delivering a medical tubular body is, for example, disclosed in Patent document 3. The Patent document 3 discloses a stent delivery catheter having an outer shaft and an inner shaft, wherein the outer shaft has dual lumens, the inner shaft has a guidewire guide tube and a pusher wire in parallel, the guidewire guide tube and the pusher wire are separately and slidably inserted into the dual lumens of the outer shaft, and the pusher wire is connected to the midpoint in the longitudinal direction of the guidewire guide tube.

RELATED ART DOCUMENT

Patent Document

Patent document 1: US 2008/0255655 A1

Patent document 2: JP 2012-45043 A

Patent document 3: JP 2012-55470 A

Patent document 4: JP 2012-115425 A

SUMMARY OF THE INVENTION

Problems to be Solved by the Invention

An example of an embodiment of a conventional medical tubular body delivering device is shown in FIG. 1. The medical tubular body delivering device has a proximal end, which is at hand of an operator, and a distal end, which is opposite to the proximal end and close to a lesion site.

FIG. 1 is a schematic cross-section view of a distal side of the medical tubular body delivering device, and the device has an outer tube 12 having a lumen in which a medical tubular body 11 is disposed, a guidewire insertion member 14 disposed proximal to the medical tubular body 11, and an inner insertion member 13 disposed in the lumen of the outer tube 12. In the guidewire insertion member 14, a penetration passage 15 through which a guidewire is to be passed is formed, a guidewire tube 16 having a lumen through which the guidewire is to be passed is disposed in the penetration passage 15, and the guidewire tube 16 extends at least to a side proximal to a proximal opening **15*a* of the penetration passage 15. The inner insertion member 13 is partially fixed to the guidewire insertion member 14, and a protection member 17 is provided outside a part of the inner insertion member 13 at a side proximal to a fixing portion 14*a* where the inner insertion member 13 and the guidewire insertion member 14 are fixed to each other. In addition, as shown in FIG. 1, the guidewire tube 16 extends to a side distal to the distal end of the guidewire insertion member 14, and the distal end of the guidewire tube 16 reaches a lumen of a distal tip 18**.

The inner insertion member 13 extends to the proximal end (to the operator's hand) of the medical tubular body delivering device, and the operation at hand can be easily transmitted to the distal side via the inner insertion member 13. By pulling the outer tube 12 to the proximal side, the medical tubular body 11 is pushed from the lumen of the outer tube 12 by the guidewire insertion member 14 to be released. In detail, when the outer tube 12 is pulled to the proximal side, the medical tubular body 11 follows the movement of the outer tube 12 and moves to the proximal side, compressing the guidewire insertion member 14 and the inner insertion member 13. When the reaction force generated in the guidewire insertion member 14 and the inner insertion member 13 against the stress of the compression exceeds the frictional resistance generated between the medical tubular body 11 and the inner surface of the outer tube 12, the medical tubular body 11 is released to the outside of the outer tube 12. However, it is known that the load to pull the outer tube 12 to the proximal side increases in situations such as when the friction resistance of the medical tubular body 11 is excessively large, when the guidewire insertion member 14 and the inner insertion member 13 are too flexible, and when these members have a structure that inhibits stress transmission in the longitudinal axis direction.

While such medical tubular body delivering device is inserted into body lumens, since the body lumens have complexly tortuous structures, the medical tubular body delivering device has to be bent to follow the tortuous body lumens. If a localized stress concentration is generated at a proximal side of the guidewire insertion member 14 when being bent, the change in stiffness of the proximal end of the guidewire insertion member 14 could cause the outer tube 12 to easily become kinked, which is a situation where it gets stuck to be unable to move. If the outer tube 12 is pulled to the proximal side w % ben it kinks, it has been impossible for the medical tubular body 11 to be released to a body lumen.

Furthermore, the inner insertion member 13 does not have enough supporting capacity because the inner insertion member 13 is slimmer than the guidewire insertion member 14. Therefore, the inner insertion member 13 may have excessive load during a process where the medical tubular body 11 is deployed. To reinforce the inner insertion member 13, it can be considered to dispose the protection member 17 outside the inner insertion member 13 as shown in FIG. 1. In this case, making a gap between the proximal end of the guidewire insertion member 14 and the distal end of the protection member 17 can improve operability, because interference between the ends of the members can be appropriately decreased, for example, when the medical tubular body delivering device is bent. However, such a gap may lead to generation of kink or increase in load for deploying the medical tubular body 11 thanks to discontinuity in stiffness. To prevent the medical tubular body delivering device from kinking, for example, it can be considered to increase the strength of the outer tube 12, which may, however, make the device difficult to follow body lumens when it passes tortuous parts or diverged parts. Thus, its contact resistance with body lumens may increase, and it is considered that the medical tubular body delivering device becomes difficult to be inserted into body lumens, which decrease operability.

An example of a catheter that is both unbreakable and flexible is disclosed in Patent document 4. The catheter includes connecting first and second tubes, a wire that diverges from the inner walls of both tubes by being supported by the connecting portion inside the two tubes, and a third tube that covers the wire and causes the portion extending from the connecting portion to deviate from the inner walls of the tubes all around. The wire, whose outer diameter is enlarged by being covered by this third tube, stops the inner wall of the narrowing second tube from moving, thereby reducing the elongation of the second tube and preventing it from breaking. However, the Patent document 4 did not consider kinking of the catheter.

The present invention has been made in response to the above situation, and the purpose of the present invention is to provide a medical tubular body delivering device that is unlikely to kink at the proximal end of a guidewire insertion member and can efficiently deploy the medical tubular body, while maintaining the reinforcing effect of an inner insertion member by a protection member without reducing operability.

Means for Solving the Problems

The present invention includes the following inventions:

[1] A medical tubular body delivering device for delivering a medical tubular body into a living body, the device comprising: an outer tube having a lumen through which the medical tubular body is disposed; a guidewire insertion member provided proximal to the medical tubular body; and an inner insertion member provided in the lumen of the outer tube, wherein the guidewire insertion member has a penetration passage through which a guidewire is to be passed; a guidewire tube having a lumen through which the guidewire is to be passed is provided in the penetration passage; the guidewire tube extends at least to a side proximal to a proximal opening of the penetration passage; the inner insertion member is partially fixed to the guidewire insertion member; a first protection member is provided outside a part of the inner insertion member at a side proximal to a fixing portion where the inner insertion member and the guidewire insertion member are fixed to each other; and at least a part of the inner insertion member between a proximal end of the fixing portion and a distal end of a region where the first protection member is provided is covered by a second protection member.

[2] The medical tubular body delivering device according to [1], wherein the second protection member is configured to movable in a longitudinal direction from a proximal side to a distal side with respect to the inner insertion member.

[3] The medical tubular body delivering device according to [1] or [2], wherein the second protection member can be reduced in length in a longitudinal direction from a proximal side to a distal side.

[4] The medical tubular body delivering device according to any one of [1] to [3], wherein a distance between a proximal end of the guidewire insertion member and a distal end of the first protection member is 30 mm or shorter.

[5] The medical tubular body delivering device according to [1], wherein the second protection member is fixed to the inner insertion member at a side proximal to the fixing portion where the inner insertion member and the guidewire insertion member are fixed to each other.

[6] The medical tubular body delivering device according to [5], wherein a proximal end of the guidewire insertion member and a distal end of the second protection member are located apart from each other in a longitudinal axis direction, and a proximal end of the second protection member and a distal end of the first protection member are located apart from each other in a longitudinal axis direction.

[7] The medical tubular body delivering device according to [1], wherein a distal end of the second protection member is fixed to a proximal end of the guidewire insertion member.

[8] The medical tubular body delivering device according to [7], wherein a distance between a proximal end of the second protection member and a distal end of the first protection member is 5 mm or shorter.

[9] The medical tubular body delivering device according to any one of [1] to [8], wherein the second protection member covers at least a part of the guidewire tube extending to a side proximal opening of the penetration passage.

[10] The medical tubular body delivering device according to any one of [1] to [9], wherein the device is of a rapid exchange type in which the outer tube has a guidewire port, wherein the guidewire port is located at a side distal to a proximal end of the outer tube.

[11] The medical tubular body delivering device according to any one of [1] to [10], wherein the guidewire tube extends to a side distal to a distal opening of the penetration passage.

[12] The medical tubular body delivering device according to [10], wherein an inner tube having a lumen through which the guidewire is to be passed is disposed in the lumen of the outer tube, and a proximal end of the inner tube is fixed to the guidewire port.

[13] The medical tubular body delivering device according to [12], wherein a part of the inner tube is disposed in the lumen of the guidewire tube.

[14] The medical tubular body delivering device according to any one of [1] to [13], wherein a proximal end part of the guidewire tube has a taper shape.

[15] The medical tubular body delivering device according to any one of [1] to [14], wherein the guidewire insertion member is colored.

[16] The medical tubular body delivering device according to any one of [1] to [15], wherein the medical tubular body is a self-expanding stent.

Effects of the Invention

According to the present invention, since at least a part of the inner insertion member between a proximal end of the fixing portion where the inner insertion member and the guidewire insertion member are fixed to each other and a distal end of a region where the first protection member is provided at a side proximal to the fixing portion is covered by the second protection member, a medical tubular body delivering device that is resistant to kinking when bent can be provided without reducing operability.

BRIEF DESCRIPTION OF THE DRAWINGS

FIG. 1 shows a cross-sectional view of an example of an embodiment of a distal side of a conventional medical tubular body delivering device.

FIG. 2 shows a schematic cross-sectional view of a first embodiment of a distal side of a medical tubular body delivering device according to the present invention.

FIG. 3 shows a cross-sectional view of a second embodiment of a distal side of a medical tubular body delivering device according to the present invention.

FIG. 4 shows a cross-sectional view of a third embodiment of a distal side of a medical tubular body delivering device according to the present invention.

FIG. 5 shows a cross-sectional view of a fourth embodiment of a distal side of a medical tubular body delivering device according to the present invention.

FIG. 6 shows a cross-sectional view of a fifth embodiment of a distal side of a medical tubular body delivering device according to the present invention.

FIG. 7 shows a cross-sectional view of a sixth embodiment of a distal side of a medical tubular body delivering device according to the present invention.

EMBODIMENTS FOR CARRYING OUT THE INVENTION

A medical tubular body delivering device according to the present invention is characterized in that the device has an outer tube having a lumen through which a medical tubular body is disposed, a guidewire insertion member provided proximal to the medical tubular body, and an inner insertion member provided in the lumen of the outer tube, wherein the guidewire insertion member has a penetration passage through which a guidewire is to be passed, a guidewire tube having a lumen through which the guidewire is to be passed is provided in the penetration passage, the guidewire tube extends at least to a side proximal to a proximal opening of the penetration passage, the inner insertion member is partially fixed to the guidewire insertion member, a first protection member is provided outside a part of the inner insertion member at a side proximal to a fixing portion where the inner insertion member and the guidewire insertion member are fixed to each other, and at least a part of the inner insertion member between a proximal end of the fixing portion and a distal end of a region where the first protection member is provided is covered by a second protection member.

Hereinafter, examples of embodiments of the medical tubular body delivering device according to the present invention will be specifically described referring to drawings, however, the present invention is not limited by the examples shown in the drawings and can be altered in design within a scope in compliance with the gist described above and below, all of which are included in the technical scope of the present invention.

FIG. 2 shows a schematic cross-sectional view of a first embodiment of a distal side of the medical tubular body delivering device according to the present invention. Note that only the distal side of the medical tubular body delivering device is shown in FIG. 2.

The medical tubular body delivering device has an outer tube 22 having a lumen through which a medical tubular body 21 is disposed, a guidewire insertion member 24 provided proximal to the medical tubular body 21, and an inner insertion member 23 provided in the lumen of the outer tube 22.

The guidewire insertion member 24 has a penetration passage 25 through which a guidewire is to be passed, a guidewire tube 26 having a lumen through which the guidewire is to be passed is provided in the penetration passage 25, and the guidewire tube 26 extends at least to a side proximal to a proximal opening 25*a* of the penetration passage 25.

The inner insertion member 23 is partially fixed to the guidewire insertion member 24, and a first protection member 27 is provided outside a part of the inner insertion member 23 at a side proximal to a fixing portion 24*a* where the inner insertion member 23 and the guidewire insertion member 24 are fixed to each other.

At least a part of the inner insertion member 23 between a proximal end 24*b* of fixing portion 24*a* and a distal end 27*a* of a region where the first protection member 27 is provided outside the inner insertion member 23 (Hereinafter, the region may be referred to as a first protection member covering region.) is covered by a second protection member 29. Hereinafter, the region between the proximal end 24*b* and the distal end 27*a* may be referred to as a second protection member covering region.

By covering at least a part of the inner insertion member 23 in the second protection member covering region with the second protection member 29, which is a different member from the first protection member 27, the space between the proximal end 24*b* of the fixing portion 24*a* and the distal end 27*a* of the first protection member covering region can be filled. By covering the inner insertion member 23 in this space with the second protection member 29, which is a different member from the first protection member 27, even if the medical tubular body delivering device is subjected to stress when it is passed through a bend in the body, the stress is distributed to both the first protection member 27 and the second protection member 29, which makes it easier to avoid localized stress concentration. That is, even if the medical tubular body delivering device is subjected to stress, the second protection member 29 behaves as a cushioning material, and the medical tubular body delivering device is less likely to kink. In addition, by filling the space between the proximal end 24*b* of the fixing portion 24*a* and the distal end 27*a* of the first protection member covering region, the support force and the insertability in the longitudinal axis direction can be improved, thus increasing the ability to support the stress applied when the medical tubular body 21 is deployed. This prevents unnecessary load from being generated when the outer tube 22 is pulled proximally to deploy the medical tubular body 21, and reduces the risk of breaking of the outer tube 22 or displacement of the medical tubular body 21 from the target site due to forceful operation, and enables easy deployment of the medical tubular body for safer treatment. Therefore, the present invention can provide a medical tubular body delivering device that is resistant to kinking even when bent without reducing operability.

From the viewpoint of filling the space between the proximal end 24*b* of the fixing portion 24*a* and the distal end 27*a* of the first protection member covering region, it can be considered that the first protection member covering region should be extended and the first protection member 27 should be disposed so that the distal end 27*a* of the region where the first protection member 27 is disposed outside the inner insertion member 23 is placed in the proximity of the proximal end 24*b* of the fixing region 24*a*. However, while operability can be improved by leaving a small gap proximal to the proximal end 24*b* of the fixing region 24*a* to moderately prevent interference between the members, this gap causes problems such as the occurrence of a kink or excessive deployment load. Accordingly, in the present invention, this gap of the inner insertion member 23 is covered by the second protection member 29, which is a different member from the first protection member 27.

The shape of the second protection member 29 may be tubular, and also may be reducible in length in the longitudinal direction. Shapes with a reducible length in the longitudinal direction includes, for example, a coiled shape and accordion shape. The tubular shape may be a mesh tube.

While the second protection member 29 may be fixed to the guidewire insertion member 24, preferably, it is not fixed to the guidewire insertion member 24. The second protection member 29 can be slidable in the longitudinal direction by not being fixed, so that stiffness in the longitudinal direction becomes continuous, which improves the kink resistance to bending and makes it less prone to kinking.

The second protection member 29 may be configured so as to be movable in the longitudinal direction with respect to the inner insertion member 23, or may be fixed to the inner insertion member 23 at a side proximal to the fixing portion 24*a* where the inner insertion member 23 and the guidewire insertion member 24 are fixed to each other.

By making the second protection member 29 unfixed to the inner insertion member 23 and movable in the longitudinal direction with respect to the inner insertion member 23, when the medical tubular body delivering device is subjected to stress, the second protection member 29 follows and moves in the longitudinal direction, so that the subjected stress is relieved and the medical tubular body delivering device is less likely to kink.

The way in which the second protection member 29 is unfixed to the inner insertion member 23 is not particularly limited, and includes, for example, a way of placing a tubular or coiled member as the second protection member 29 in an unfixed state at a side distal to the part of the inner insertion member 23 where the first protection member 27 is disposed outside, and then inserting a distal end part of the inner insertion member 23 into the guidewire insertion member 24 to fix the inner insertion member 23 and the guidewire insertion member 24 to each other; or a way of inserting a distal end part of the inner insertion member 23 where the first protection member 27 is disposed outside into the guidewire insertion member 24 to fix them, and then inserting a tubular member with a C-shaped cross section as the second protection member 29 between the proximal end 24*b* of the fixing region 24*a* and the distal end of the region where the first protection member 27 is placed.

In the case where the second protection member 29 is configured so as to be movable in the longitudinal direction with respect to the inner insertion member 23, a distance x between the distal end 27*a* of the first protection member 27 and the proximal end 24*b* of the fixing region 24*a* is preferably, for example, 30 mm or shorter. A distance x of 30 mm or shorter makes the medical tubular body delivering device have continuous stiffness in the longitudinal direction, which improves its kink resistance to bending and makes it less prone to kink. Furthermore, the continuous stiffness in the longitudinal direction of the medical tubular body delivering device allows a smoother transfer of stress from the guidewire insertion member 24 during the deployment of the medical tubular body 21, thus preventing unnecessary load generation during the deployment operation of the medical tubular body 21. Accordingly, it is desirable for the distance x to be as short as possible. The distance x is more preferably 20 mm or shorter, even more preferably 10 mm or shorter, and especially preferably 5 mm or shorter. By setting the distance x to 5 mm or shorter, the first protection member 27 can improve supportability and insertability of the inner insertion member 23, and can support the stress from the guidewire insertion member 24 in unison with the inner insertion member 23 when the medical tubular body 21 is deployed. The lower limit of the distance x is not particularly limited, however, if it is too short, the guidewire insertion member 24 and the distal end of the first protection member 27 are likely to come into contact with each other, and the distal end part of the first protection member 27 may be bent and damaged by stress from the guidewire insertion member 24, so that the distance x is preferably 1 mm or longer, and more preferably 2 mm or longer.

On the other hand, by fixing the second protection member 29 to the inner insertion member 23, it is possible to improve supportability and insertability in the longitudinal direction, thus increasing the ability to support the stress applied when deploying the medical tubular body 21.

In the case where the second protection member 29 is fixed to the inner insertion member 23, the second protection member 29 is preferably disposed so that a proximal end of the guidewire insertion member 24 and a distal end of the second protection member 29 are located apart from each other in the longitudinal axis direction, and a proximal end of the second protection member 29 and a distal end of the first protection member are located apart from each other in the longitudinal axis direction. Such a configuration can moderately prevent interference between the members, thus improving operability.

The way in which the second protection member 29 is fixed to the inner insertion member 23 is not particularly limited, and includes, for example, a way of fixing the second protection member 29, which is a different member from the first protection member 27, at a side distal to the part of the inner insertion member 23 where the first protection member 27 is disposed outside, and then inserting a distal end part of the inner insertion member 23 into the guidewire insertion member 24 to fix them, or a way of inserting a distal end part of the inner insertion member 23 where the first protection member 27 is disposed outside into the guidewire insertion member 24 to fix them, and then inserting a tubular member with a C-shaped cross section as the second protection member 29 between the proximal end of the fixing portion and the distal end of the region where the first protection member 27 is placed to fix the second protection member 29 and the inner insertion member 23 by adhesive, fusion, or the like.

The material of the second protection member 29 may be the same or different from that of the first protection member 27, however, in order to avoid stress concentration in the vicinity of the second protection member 29 to cause kinking, the stiffness of the second protection member 29 is preferably higher than the stiffness of the first protection member 27.

The guidewire insertion member 24 is provided with a penetration passage 25 through which a guidewire is to be passed, and a guidewire tube 26 having a lumen through which the guidewire is to be passed is disposed in the penetration passage 25. The guidewire tube 26 allows the guidewire to be inserted into the lumen, so that the medical tubular body delivering device can be easily inserted into the body lumen along the inserted guidewire. The inner wall of the penetration passage 25 and the outer wall of the guidewire tube 26 may be, for example, fixed to each other by thermal fusion or adhesive and the like.

The guidewire tube 26 extends at least to a side proximal to a proximal opening 25*a* of the penetration passage 25. The proximal end of the guidewire tube 26 protrudes proximally from the proximal end of the penetration passage 25, so that the change in stiffness at the proximal end of the guidewire insertion member becomes continuous, which improves the operability of the medical tubular body delivering device.

The shape of the proximal end part of the guidewire tube 26 is not particularly limited, and may be, for example, perpendicular to the longitudinal axis direction as shown in FIG. 2, or tapered, concavo-convex, stair-stepped, corrugated, and the like. The tapered shape is more preferable. The tapered shape improves the continuity of the change in stiffness to easily prevent kinking.

The guidewire tube 26 may extends to a side distal to the distal opening 25*b* of the penetration passage 25, and the distal end of the guidewire tube 26 may extends into a lumen of a distal tip 28 as shown in FIG. 2.

The inner insertion member 23 is partially fixed to the guidewire insertion member 24. The inner insertion member 23 may be press-fitted into the guidewire insertion member 24, or may be fixed to the guidewire insertion member 24 by thermal fusion or adhesive.

The first protection member 27 is provided outside a part of the inner insertion member 23 at a side proximal to the fixing portion 24*a*. By providing the first protection member 27 outside a part of the inner insertion member 23 in the above-described region, damage to the inner insertion member 23 can be prevented. In addition, by providing the first protection member 27, supportability and insertability of the inner insertion member 23 in the longitudinal axis direction can be improved, thus increasing the ability to support the stress applied when deploying the medical tubular body, so that the medical tubular body can be easily deployed. Preferably, the first protection member 27 is in contact with the inner insertion member 23 to cover the inner insertion member 23.

An extrusion member may be placed at the distal end of the guidewire insertion member 24 to facilitate extrusion of the medical tubular body 21.

The guidewire insertion member 24 is preferably colored. By coloring the guidewire insertion member 24, it is easier to see it under the endoscope and to check the position of the guidewire insertion member 24. The colored guidewire insertion member 24 is sometimes referred to as a visual marker. The color to be applied to the guidewire insertion member 24 is not particularly limited as long as it is easily visible under the endoscope, but for example, a color that is relatively conspicuous against the mucosa and blood in the gastrointestinal tract is preferred, and yellow is particularly preferred.

Materials constituting the guidewire insertion member 24, the outer tube 22, the first protection member 27, and the second protection member 29 include, for example, resin materials such as polyethylene, fluorine resin (for example, polytetrafluoroethylene (PTFE), tetrafluoroethylene/perfluoroalkyl vinyl ether copolymer (PFA) etc.), polyamide, polyamide-based elastomer, polyurethane, polyester, silicone, polyether ether ketone (PEEK).

Materials constituting the inner insertion member 23 include, for example, various metallic materials such as stainless steel, nickel-titanium alloys, tungsten, gold, and platinum.

Next, a second embodiment of the distal side of the medical tubular body delivering device according to the present invention will be described referring to FIG. 3. In FIG. 3, the same part as in the above drawing is marked with the same reference sign to avoid redundant explanation (the same, hereinafter).

As shown in FIG. 3, the second protection member 29 may cover at least a part of the guidewire tube 26 extending to a side proximal to a proximal opening 25*a* of the penetration passage 25. By covering at least a part of the guidewire tube 26 and a part of the inner insertion member 23 with the unfixed second protection member 29 to restrain them, the space between the proximal end 24*b* of the fixing portion 24*a* and the distal end 27*a* of the first protection member covering region can be filled with the second protection member 29. In addition, the guidewire tube 26 and the inner insertion member 23 can be integrated so that the positional relationship between them does not deviate, which can further improve supportability and insertability in the longitudinal axis direction, and further increase the ability to support the stress applied when the medical tubular body 21 is deployed. By making the second protection member 29 unfixed, it is possible for the second protection member 29 to move in the longitudinal direction and disperse the stress appropriately.

The shape of the proximal end part of the second protection member 29 may be, for example, tapered. Such a configuration improves the continuity in stiffness to the first protection member 27, which improves the deliverability and suppresses the operational load during deployment of the medical tubular body 21.

Next, a third embodiment of the distal side of the medical tubular body delivering device according to the present invention will be described referring to FIG. 4. As shown in FIG. 4, the distal end of the second protection member 29 may be fixed to the proximal end of the guidewire insertion member 24. By fixing the second protection member 29 to the guidewire insertion member 24, the continuity of the stiffness change from the guidewire insertion member can be improved, so that supportability and insertability in the longitudinal axis direction can be further improved, and further increase the ability to support the stress applied when the medical tubular body 21 is deployed. The second protection member 29 and the guidewire insertion member 24 may be, for example fixed to each other by thermal fusion or adhesive.

While an example in which the second protection member 29 covers only the inner insertion member 23 is shown in FIG. 4, the present invention is not limited to the configuration, and as shown in FIG. 3, the second protection member 29 may cover the inner insertion member 24 and at least a part of the guidewire tube 26, and the distal end of the second protection member 29 may be fixed to the proximal end of the guidewire insertion member 24.

A distance y between the distal end 27*a* of the first protection member 27 and the proximal end 29*a* of the second protection member 29 is preferably 5 mm or shorter, for example. By making the distance y 5 mm or shorter, the stiffness in the longitudinal axis direction of the medical tubular body delivering device becomes continuous, which improves its resistance to bending and makes it less prone to kinking. The shorter the distance y, the better. The distance y is more preferably 4 mm or shorter, even more preferably 3 mm or shorter, and especially preferably 2 mm or shorter. By setting the distance y to 2 mm or shorter, the first protection member 27 can improve the supportability and insertability of the inner insertion member 23, and can support the stress from the guidewire insertion member 24 in unison with the inner insertion member 23 when the medical tubular body 21 is deployed. The distance y between the distal end 27*a* of the first protection member 27 and the proximal end 29*a* of the second protection member 29 may be 1 mm or longer, for example.

Next, a fourth embodiment of the distal side of the medical tubular body delivering device according to the present invention will be described referring to FIG. 5. As shown in FIG. 5, the medical tubular body delivering device may be of a rapid exchange type in which the outer tube 22 has a guidewire port 31, and the guidewire port 31 is preferably located at a side distal to the proximal end of the outer tube 22.

The proximal end side of the guidewire tube 26 may extend to the guidewire port 31.

While the rapid exchange type is shown in FIG. 5 as other embodiment of the medical tubular body delivering device, the device may be of an over-the-wire type.

Next, a fifth embodiment of the distal side of the medical tubular body delivering device according to the present invention will be described referring to FIG. 6. As shown in FIG. 6, an inner tube 51 having a lumen through which the guidewire is to be passed may be disposed in the lumen of the outer tube 22, and the proximal end of the inner tube 51 may be fixed to the guidewire port 31.

Embodiments in which the proximal end of the inner tube 51 is fixed to the guidewire port 31 include, for example, an embodiment in which the outer tube 22 is partly thick-walled to form a filling member 30 between it and the inner tube 51, and the outer tube 22 and the proximal end part of the inner tube 51 are fixed without gaps; an embodiment in which a filling member 30 made of resin or the like is interposed between the proximal end part of the inner tube 51 and the outer tube 22 to fix them with an adhesive; and an embodiment in which the proximal end part of the inner tube 51 and the outer tube 22 are adhered with an adhesive as an filling member 30. Alternatively, included is an embodiment in which not using the filling member 30, an inner wall of the outer tube 22 and an outer wall of the inner tube 51 are in close contact with each other to fix them, for example, by thermal fusion or crimping.

The embodiment of the medical tubular body delivering device shown in FIG. 6 is preferably of a rapid exchange type.

As shown in FIG. 6, a part of the inner tube 51 may be disposed in the lumen of the guidewire tube 26. Such a configuration prevents the guidewire from becoming entangled in, for example, the inner insertion member 23 to become inoperable or impede the release of the medical tubular body 21, because the guidewire is always positioned in the lumen of the inner tube 51 or the penetration passage 25 when the outer tube 22 is pulled proximally to release and deploy the medical tubular body 21.

Next, a sixth embodiment of the distal side of the medical tubular body delivering device according to the present invention will be described referring to FIG. 7. The medical tubular body delivering device shown in FIG. 7 is configured such that the guidewire tube 26 having a lumen through which the guidewire is to be passed is disposed in the penetration passage 25, the distal end of the guidewire tube 26 extends to the distal tip 28, and the proximal side of the guidewire tube 26 extends to the proximal opening 25*a* of the penetration passage 25. The shape of the proximal end part of the guidewire tube 26 is tapered. The tapered shape makes it easier to prevent kinking. The continuity in stiffness change from the guidewire insertion member 24 to the second protection member 29 and the first protection member 27 becomes improved, so that the continuity in stiffness change of the medical tubular body delivering device as a whole becomes improved, which makes it easier for the medical tubular body delivering device to be prevented from kinking.

In addition, the inner tube 51 having a lumen through which the guidewire is to be passed is disposed in the lumen of the outer tube 22, the proximal end of the inner tube 51 is fixed to the guidewire port 31, and the inner tube 51 extends to the distal tip 28 through the lumen of the guidewire tube 26 disposed in the penetration passage 25.

FIG. 7 shows a configuration in which the filling member 30 is interposed between the inner tube 51 and the outer tube 22. The shape of the proximal end part of the filling member 30 matches the shape of the proximal end part of the inner tube 51. By matching the shape of the proximal end part of the filling member 30 with the shape of the proximal end part of the inner tube 51, the integrity of the outer surface of the outer tube is improved, which facilitates the delivery operation.

As shown in FIG. 7, a locking member 32 may be disposed on the outer surface of the guidewire tube 26. The locking member 32 engages the inner surface of the medical tubular body 21, and when the outer tube 22 is pulled proximally, the medical tubular body 21 is restrained from retracting by the locking member 32 and is deployed outwards from the outer tube 22.

The position where the locking member 32 is placed is not particularly limited as long as the retraction of the medical tubular body 21 can be prevented, and for example, a position proximal to the central position in the longitudinal axis direction of the medical tubular body 21 is preferable. Alternatively, the proximal end of the medical tubular body 21 may be supported by the distal end of the guidewire insertion member 24 without the locking member 32.

As the medical tubular body, for example, stents, stent grafts, occlusive devices, injection catheters, prosthesis valves, and the like can be used. Of these, stents are preferable. Stents includes, for example, coiled stents made of single wire metal or polymeric materials, stents made of metal tubes cut out by a laser, stents made of metal sheets cut out by a laser and then wound into a cylindrical shape and laser welded, stents made of linear components welded together by a laser, and stents made of several woven wire metals. Stents are classified as either balloon expandable stents, which are expanded by a balloon mounting the stent, or self-expandable stents, which expand themselves by removing an external component that inhibits the expansion of the stent. In the present invention, the self-expandable stents are preferably used.

The present application claims priority based on Japanese Patent Application No. 2019-228671 filed on Dec. 18, 2019. All the contents described in Japanese Patent Application No. 2019-228671 filed on Dec. 18, 2019 are incorporated herein by reference.

DESCRIPTION OF REFERENCE SIGNS

- 11, 21: medical tubular body
- 12, 22: outer tube
- 13, 23: inner insertion member
- 14, 24: guidewire insertion member

14*a*: fixing portion
15, 25: penetration passage
15*a*: proximal opening of the penetration passage 15
16, 26: guidewire tube
17: protection member
18, 28: distal tip
24*a*: fixing portion where the inner insertion member 23 and the guidewire insertion member 24 are fixed to each other
24*b*: proximal end of the fixing portion 24*a*
25*a*: proximal opening of the penetration passage 25
25*b*: distal opening of the penetration passage 25
27: first protection member
27*a*: distal end of the first protection member
29: second protection member
29*a*: proximal end of the second protection member
30: filling member
31: guidewire port
32: locking member
51: inner tube

The invention claimed is:

1. A medical tubular body delivering device for delivering a medical tubular body into a living body, the medical tubular body delivering device comprising:

an outer tube extending from a proximal side to a distal side and having a lumen through which the medical tubular body is disposed;

a guidewire insertion member provided in the lumen of the outer tube and proximal to the medical tubular body;

an inner insertion member provided in the lumen of the outer tube;

a guidewire tube having a lumen through which a guidewire is to be passed;

a first protection member; and a second protection member, wherein the guidewire insertion member has a penetration passage, the guidewire tube and the guidewire insertion member are configured so that the guidewire tube is disposed in the penetration passage of the guidewire insertion member and the guidewire tube protrudes from a proximal opening of the penetration passage toward the proximal side, the inner insertion member is partially fixed to the guidewire insertion member at a fixing portion, the guidewire insertion member, the inner insertion member, the first protection member, and the second protection member are configured so that a proximal portion of the inner insertion member is covered by the first protection member and a distal portion of the inner insertion member is covered by the second protection member, and the second protection member is disposed between the fixing portion and the first protection member in a longitudinal direction from the proximal side to the distal side, and the second protection member is configured so that length of the second protection member is reducible in the longitudinal direction from the proximal side to the distal side.

2. The medical tubular body delivering device according to claim 1, wherein the second protection member is configured to be movable in the longitudinal direction from the proximal side to the distal side with respect to the inner insertion member.

3. The medical tubular body delivering device according to claim 1, wherein a distance between a proximal end of the guidewire insertion member and a distal end of the first protection member is 30 mm or shorter.

4. The medical tubular body delivering device according to claim 1, wherein the second protection member is fixed to the inner insertion member at a side proximal to the fixing portion where the inner insertion member and the guidewire insertion member are fixed to each other.

5. The medical tubular body delivering device according to claim 4, wherein a proximal end of the guidewire insertion member and a distal end of the second protection member are located apart from each other in a longitudinal axis direction, and a proximal end of the second protection member and a distal end of the first protection member are located apart from each other in the longitudinal axis direction.

6. The medical tubular body delivering device according to claim 1, wherein a distal end of the second protection member is fixed to a proximal end of the guidewire insertion member.

7. The medical tubular body delivering device according to claim 6, wherein a distance between a proximal end of the second protection member and a distal end of the first protection member is 5 mm or shorter.

8. The medical tubular body delivering device according to claim 1, wherein the second protection member is disposed so as to cover a part of the guidewire tube protruding from the proximal opening of the penetration passage of the guidewire insertion member.

9. The medical tubular body delivering device according to claim 1, wherein the device is of a rapid exchange type in which the outer tube has a guidewire port, wherein the guidewire port is located at a side distal to a proximal end of the outer tube.

10. The medical tubular body delivering device according to claim 9, further comprising an inner tube having a lumen through which the guidewire is to be passed, wherein the inner tube is disposed in the lumen of the outer tube, and a proximal end of the inner tube is fixed to the guidewire port.

11. The medical tubular body delivering device according to claim 10, wherein a part of the inner tube is disposed in the lumen of the guidewire tube.

12. The medical tubular body delivering device according to claim 1, wherein the guidewire tube is disposed in the penetration passage of the guidewire insertion member so that the guidewire tube protrudes from a distal opening of the penetration passage toward the distal side.

13. The medical tubular body delivering device according to claim 1, wherein a proximal end part of the guidewire tube has a taper shape.

14. The medical tubular body delivering device according to claim 1, wherein the guidewire insertion member is colored.

15. The medical tubular body delivering device according to claim 1, wherein the medical tubular body is a self-expanding stent.

* * * * *